United States Patent
Parola et al.

(10) Patent No.: US 6,936,721 B2
(45) Date of Patent: Aug. 30, 2005

(54) METALLIC THIACALIX[4]ARENE COMPLEXES

(75) Inventors: Stephane Parola, Jonage (FR); Cedric Desroches, Lyons (FR); Francis Vocanson, Aurec sur Loire (FR); Jean Bouix, Lyons (FR); Roger Lamartine, Villeurbanne (FR)

(73) Assignees: Universite Claude Bernard Lyon 1, Villeurbanne Cedex (FR); Centre National de la Recherche Scientifique (C.N.R.S.), Paris Cedex (FR)

( * ) Notice: Subject to any disclaimer, the term of this patent is extended or adjusted under 35 U.S.C. 154(b) by 0 days.

(21) Appl. No.: 10/468,008

(22) PCT Filed: Feb. 25, 2002

(86) PCT No.: PCT/FR02/00685

§ 371 (c)(1),
(2), (4) Date: Feb. 10, 2004

(87) PCT Pub. No.: WO02/068521

PCT Pub. Date: Sep. 6, 2002

(65) Prior Publication Data

US 2004/0127722 A1 Jul. 1, 2004

(30) Foreign Application Priority Data

Feb. 23, 2001 (FR) .............................. 01 02464

(51) Int. Cl.$^7$ ............................. C07D 495/22

(52) U.S. Cl. ............................. 549/3; 549/11

(58) Field of Search ....................... 549/3, 11

(56) References Cited

U.S. PATENT DOCUMENTS

| 4,018,807 A | 4/1977 | Brooks, Jr. |
| 4,885,114 A | 12/1989 | Gordon et al. |
| 5,116,113 A | 5/1992 | Chu |

FOREIGN PATENT DOCUMENTS

| EP | 0375898 | 7/1990 |
| EP | 0731102 | 9/1996 |
| JP | 10077281 | 3/1998 |
| JP | 11130770 | 5/1999 |

OTHER PUBLICATIONS

Higuchi et al, "Fluorescent Chemo–Sensor for Metal Cations Based . . . Lower Rim" Tetrahedron, NL, Elsevier Science Publishers, vol. 56, No. 27, Jun. 2000, pp. 4659–4666, XP004206693.

Narita et al "Metal Sensor of Water Soluble Dansyl–Modified . . . arenes" Tetrahedron Letters, NL, Elsevier Science Publishers, vol. 39, No. 47, Nov. 1998, pp. 8687–8690, XP004140616.

Lhotak et al "Tetraalkylated 2,8,14,20–Tetrathiacalix . . . Novel Infinite Channels in the Solid State" Tetrahedron Letters, NL, Elsevier Science Publishers, vol. 39, No. 48, Nov. 1998, pp. 8915–8918, XP004140964.

Lhotak et al "NMR and X–ray Analysis of 25,27–Dimethoxythiacalix . . . Unique Infinite Channels in the Solid State" Tetrahedron Letters, Elsevier Science Publishers, vol. 41, No. 48, Nov. 2000, pp. 9339–9344, XP004236245.

Bouoit–Montesinos et al "Synthesis of New Phenylazocalix . . . " Tetrahedron Letters, NL, Elsevier Science Publishers, vol. 41, No. 15, Apr. 2000, pp. 2563–2567, XP004194552.

Mlika et al "Calixarene Membranes on Semiconductor Substrates for E.I.S. Chemical Sensors" Electrochimica Acta, GB, Elsevier Science Publishers Barking, 1998, vol. 43, No. 8, pp. 841–847.

Ali et al "Comparison of Thiacalix . . . for Copper Ion detection" Chem. Abstracts Service, 2000, XP002172647.

*Primary Examiner*—Bernard Dentz
(74) *Attorney, Agent, or Firm*—Dennison, Schultz, Dougherty & MacDonald

(57) ABSTRACT

The object of the invention is new complexes of derivatives of thiacalix[4]arenes having the formula:

(I)

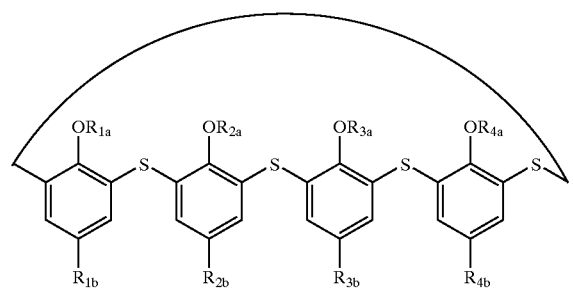

$R_{1a}$, $R_{2a}$, $R_{3a}$, $R_{4a}$, $R_{1b}$, $R_{2b}$, $R_{3b}$ et $R_{4b}$ are such as defined in claim 1 and their utilization, especially for manufacturing of materials having optical limiter properties.

16 Claims, No Drawings

METALLIC THIACALIX[4]ARENE COMPLEXES

This application is a 371 of PCT/FR02/00685, filed on Feb. 25, 2002.

The present invention relates to novel metallic complexes of thiacalix[4]arenes, in particular with a transition metal, as well as their utilization, especially in the manufacture of materials having optical limiter properties.

Certain thiacalixarene derivatives are described in the prior art: For example, the patent application published under number WO 99 19 427 can be cited, in which the derivatives of formula (A) are described:

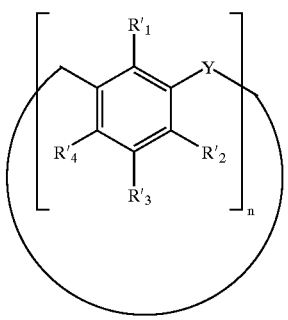

(A)

wherein Y is a divalent bridging group, at least one of said bridging groups being a sulfur atom, $R'_3$ is hydrogen, a hydrocarbyl group or a hydrocarbyl hetero-substituted hydrocarbyl group and is an integer at least equal to 4.

It will be noted that the sole example of compound (A) given is a dodecylcalix[8]arene containing sulfur. Moreover, it is indicated that the derivatives of formula (A) are used as additives in lubricating oil compositions.

Other derivatives of thiacalix[4]arene are described in the literature: Lhotak et al describes in Tetrahedron Letters 2000, 41, 9339–9344, in particular 25,27 dimethoxythiacalix[4]arene and in Tetrahedron Letters 1998, 39, 8915–8918, derivatives of thiacalix[4]arenes of formula (B):

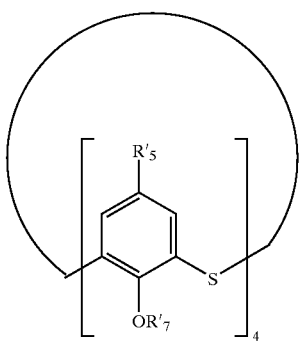

(B)

wherein $R'_5$ is an atom of hydrogen or a tert-butyl group and $R'_7$ is a methyl, ethyl, n-propyl or n-butyl group. In the solid phase, these different compounds form infinite chains.

One of the objects proposed by the invention is the production of new derivatives of thiacalix[4]arenes having in particular the following properties:
  good electronic delocation of electrons π;
  high complexing properties;
  high thermal stability, which makes possible thermal treatment of these compounds and thus their incorporation in materials such as in a vitreous matrix, for example.

These compounds are functionalized or easily functionalized, which makes it possible to modulate their properties.

The thiacalix[4]arenes according to the invention and their metal complexes have non-linear, third-order optical properties. It should be noted that laser technology has seen recent and rapid progress resulting in the appearance of novel compact, performance laser systems operating at variable wavelengths. Also, elaboration of novel materials is necessary that make it possible to safeguard equipment, optical sensors and the operator's eyes against the harmful effects of lasers.

Certain complexes of the thiacalix[4]arenes according to the invention with a transition metal have thermochrome properties.

The present invention concerns the thiacalix[4]arenes having the formula (I):

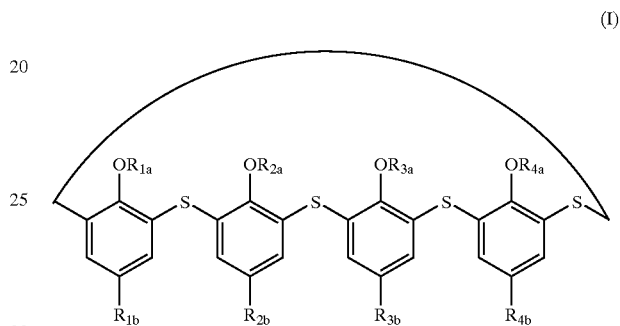

(I)

wherein:
Being the same or different, $R_{1a}$, $R_{2a}$, $R_{3a}$ et $R_{4a}$ each independently being:
  a hydrogen atom;
  a $(C_1-C_{12})$ alkyl group:
  a $(C_1-C_{12})$ alcenyl group;
  an $SO_2$—$R_1$ group, wherein $R_1$ is a phenyl, benzyl or naphthyl group, singly or multiply substituted or unsubstituted by a halogen atom, a $(C_1-C_4)$ alkyl, $(C_1-C_4)$ alcenyl or $(C_1-C_4)$ alcynyl group, or even a $SiR_2R_3R_4$ group, wherein $R_2$, $R_3$ and $R_4$ each independently is a $(C_1-C_4)$ alkyl group;

$R_{1b}$, $R_{2b}$, $R_{3b}$ et $R_{4b}$, being the same or different, each being independently:
  an atom of hydrogen;
  a halogen atom;
  a $(C_1-C_6)$ alkyl group:
  a phenylazo group, eventually preferably substituted at position 4 by a nitro group;
  a —N═$CHR_5$ group, wherein $R_5$ is a $(C_1-C_4)$ alkyl, pyridyl or phenyl group;
  a —C≡C—$R_6$ group, wherein $R_6$ is a hydrogen atom, a $(C_1-C_4)$ alkyl, tri-$(C_1-C_4)$-alkylsilyl, phenyl group, or a group having the formula:

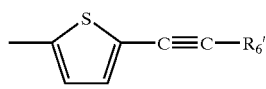

wherein $R'_6$ is a hydrogen atom a phenyl eventually substituted in para by a $(C_1-C_6)$ alkyl group;
a nitro group, or even
a —$NR_7R_8$ group, wherein $R_7$ is a hydrogen atom and $R_8$ is a hydrogen atom or a —$C(O)R_5$ group with $R_5$ chosen from the group comprising $(C_1-C_4)$ alkyl, pyridyl or phenyl;

it being understood that, when at least one of the $R_{1a}$, $R_{2a}$, $R_{3a}$ and $R_{4a}$ groups is a methyl group, the others are a hydrogen atom or when $R_{1a}=R_{2a}=R_{3a}=R_{4a}$ and is either a $(C_2–C_4)$ alkyl or a hydrogen atom, then one at least of the substituents $R_{1b}$, $R_{2b}$, $R_{3b}$ or $R_{4b}$ is different from hydrogen or from the tert-butyl group;

as well as their salts, solvates and hydrates.

An alkyl is defined as a monovalent linear or branched saturated hydrocarbon radical.

An alcenyl is defined as a monovalent linear or branched unsaturated hydrocarbon radical comprising a double bond.

An alcynyl is defined as a monovalent linear or branched unsaturated hydrocarbon radical comprising a triple bond.

A $(C_1–C_4)$ alkyl is defined as an alkyl radical comprising from 1 to 4 carbon atoms.

A halogen atom is defined as an atom of chlorine, bromine, iodine or fluorine.

It will be noted that the exclusion introduced in the definition of the compounds having formula (I) has the particular purpose of excluding the compounds already described in the prior art; that is, in Tetrahedron Letters 1998, 39, 8915–8918 and 2000, 41, 9339–9344.

According to another of its aspects, the present invention is related to the compounds of formula (I), in which:

$R_{1a}$, $R_{2a}$, $R_{3a}$ et $R_{4a}$, being the same or different, each being independently:
a hydrogen atom;
a $(C_1–C_{12})$ alkyl group;
a $(C_1–C_{12})$ alcenyl group, or
a —$SiR_2R_3R_4$ group, wherein $R_2$, $R_3$ and $R_4$ each independently is a $(C_1–C_4)$ alkyl group;

$R_{1b}$, $R_{2b}$, $R_{3b}$ and $R_{4b}$, being the same or different, each independently is:
a hydrogen atom
a halogen atom
a $(C_1–C_6)$ alkyl group;
a —N=$CHR_5$ group, in which $R_5$ is a $(C_1–C_4)$ alkyl, pyridyl or phenyl group;
a —C≡C—$R_6$ group, in which $R_6$ is a hydrogen atom; a $(C_1–C_4)$ alkyl, tri$(C_1–C_4)$alkylsilyl, phenyl group or a group having the formula:

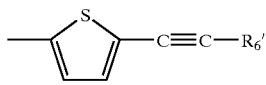

where $R_6'$ is a hydrogen atom or a phenyl possibly with a para substitution with a $(C_1–C_6)$ alkyl group;
a nitro group, or
a —$NR_7R_8$ group, in which $R_7$ is a hydrogen atom and $R_8$ is a hydrogen atom or a —$C(O)R_5$ group with $R_5$ being chosen from the group comprising a $(C_1–C_4)$ alkyl, pyridyl or phenyl group;

it being understood that, when one at least of the groups $R_{1a}$, $R_{2a}$, $R_{3a}$ or $R_{4a}$ groups is a methyl group, the others are a hydrogen atom or when $R_{1a}=R_{2a}=R_{3a}=R_{4a}$ and is either a $(C_2–C_4)$ alkyl group or a hydrogen atom, when one at least of the $R_{1b}$, $R_{2b}$, $R_{3b}$ or $R_{4b}$ substituents is different from hydrogen or from the tert-butyl group.

as well as their salts, solvates and hydrates.

According to another of its aspects, the present invention is related to the compounds of formula (I), in which:

$R_{1a}$, $R_{2a}$, $R_{3a}$ et $R_{4a}$, being the same or different, each is independently:
a hydrogen atom
a $(C_1–C_6)$ alkyl group;
a —$SO_2$—$R_1$ group, in which $R_1$ is a phenyl group, substituted or unsubstituted by a $(C_1–C_4)$ alkyl group, or
a —$SiR_2R_3R_4$ group, in which $R_2$, $R_3$ et $R_4$ each independently is a $(C_1–C_4)$ alkyl group;

$R_{1b}$, $R_{2b}$, $R_{3b}$ et $R_{4b}$, being the same or different, each independently is:
a hydrogen atom
a halogen atom
a $(C_1–C_6)$ alkyl group;
a phenylazo group possibly substituted preferably at position 4 by a nitro group;
a —N=$CHR_5$ group, in which $R_5$ is a pyridyl group;
a —C≡C—$R_6$ group, in which $R_6$ is a hydrogen atom or a phenyl group, or a group having the formula:

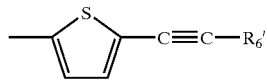

where $R_6'$ is a hydrogen atom or a phenyl possibly with a para substitution with a $(C_1–C_6)$ alkyl group;
a nitro group, or
—$NR_7R_8$ group, in which $R_7$ is a hydrogen atom and $R_8$ is a hydrogen atom or a benzoyl group;

it being understood that, when one at least of the groups $R_{1a}$, $R_{2a}$, $R_{3a}$ and $R_{4a}$ groups are(s) a methyl group, the others are a hydrogen atom or when $R_{1a}=R_{2a}=R_{3a}=R_{4a}$ and are either a $(C_2–C_4)$ alkyl group or a hydrogen atom, when one at least of the $R_{1b}$, $R_{2b}$, $R_{3b}$ or $R_{4b}$ substituents is different from hydrogen or from the tert-butyl group;

as well as their salts, solvates and hydrates.

The compounds having formula (I), wherein one at least of the $R_{1b}$, $R_{2b}$, $R_{3b}$ et $R_{4b}$ substituents is a —N=$CHR_5$, —$NR_7R_8$ or nitro group, in which $R_7$ is a hydrogen atom and $R_8$ is a hydrogen atom or a —$C(O)R_5$ group with $R_5$ being chosen from the group comprising a $(C_1–C_4)$ alkyl, pyridyl or phenyl group, as well as their salts, solvates or hydrates, are an other aspect of the present invention.

The object of the present invention is likewise the thiacalix[4]arenes having the formula (Ia):

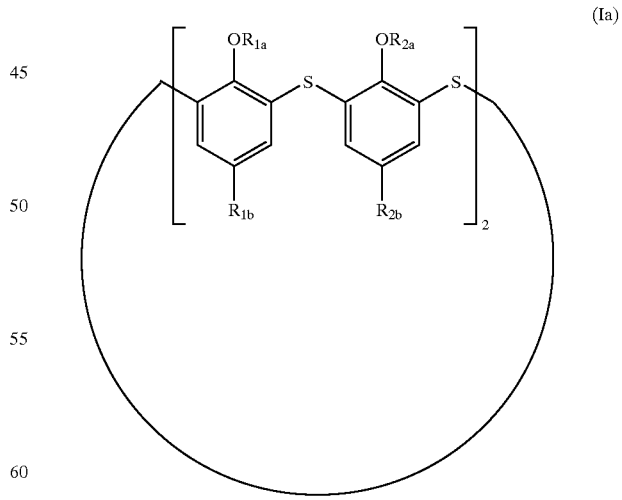

in which $R_{1a}$, $R_{2a}$, $R_{1b}$ and $R_{2b}$ are as hereinbefore defined, as well as their salts, solvates or hydrates.

The present invention similarly utilizes the thiacalix[4] arenes having the formula (Ia), in which $R_{1a}$ is a hydrogen atom or a $(C_1–C_{12})$ alkyl or $(C_1–C_{12})$ alcenyl group and $R_{2a}$ is a hydrogen atom or a ($C_1$–$C_{12}$) alkyl group, ($C_1$–$C_{12}$) alcenyl, —$SO_2$—$R_1$ group or —$SiR_2R_3R_4$; $R_1$, $R_2$, $R_3$ et $R_4$ being such as hereinbefore described, as well as their salts, solvates and hydrates.

According to another of its aspects, the invention is related to thiacalix[4]arenes having the formula (Ib):

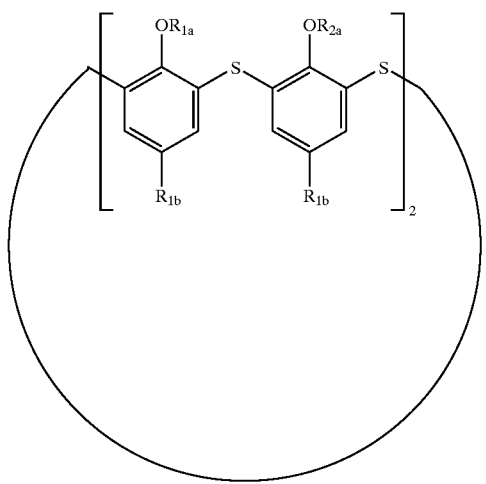

(Ib)

in which $R_{1a}$, $R_{2a}$ and $R_{1b}$ are such as hereinbefore described for (I) and (Ia), as well as their salts, solvates and hydrates.

According to yet another aspect, the invention concerns the derivatives of thiacalix[4]arenes having the formula (Ic):

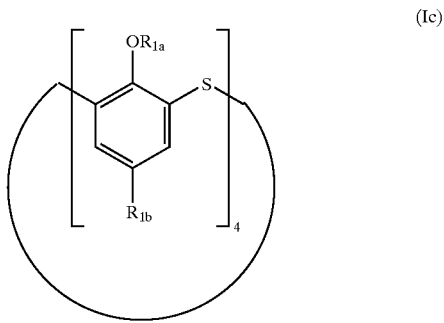

(Ic)

in which $R_{1a}$ and $R_{1b}$ are such as hereinbefore described for (I) and (Ia), as well as their salts, solvates and hydrates.

The object of the present invention is likewise the thiacalix[4]arenes chosen from the group comprising:

5,11,17,23-tetraiodo-25,26,27,28-tetrahydroxythiacalix[4]arene, 5,11,17,23-tetraiodo-25,26,27,28-tetrahydroxythiacalix[4]arene, 5,11,17,23-tetra(tert-butyl)-25-propoxy-26,27,28-trihydroxythiacalix[4]arene, 5,11,17,23-tetra(tert-butyl)-25,27-di(tert-butyldimethylsiloxy)-26,28-dihydroxythiacalix[4]arene, 5,11,17,23-tetra(tert-butyl)-25,26,27,28-tetrahexyloxythiacalix[4]arene, 5,11,17,23-tetrakis(phenylazo)-25,26,27,28-tetrahydroxythiacalix[4]arene, 5,11,17,23-tetrakis(4-nitrophenylazo)-25,26,27,28-tetrahydroxythiacalix[4]arene, 5,11,17,23-tetra(tert-butyl)-25,27-di(4-toluenesulfonyloxy)-26,28-di-hydroxythiacalix[4]arene, 5,11,17,23-tetranitro-25,26,27,28-tetrahydroxythiacalix[4]arene, tetrachlorhydrate of 5,11,17,23-tetramino-25,26,27,28-tetrahydroxythiacalix[4]arene, 25,27-di(4-toluenesulfonyloxy)-26,28-dihydroxythiacalix[4]arene, 25,27-di(tert-butyldimethylsiloxy)-26,28-dihydroxythiacalix[4]arene, 5,11,17,23-tetrakis(phenylazo)-25,27-di(4-toluenesulfonyloxy)-26,28-dihydroxythiacalix[4]arene, 5,11,17,23-tetrakis(4-nitrophenylazo)-25,27-di(4-toluenesulfonyloxy)-26,28-dihydroxythiacalix[4]arene, 5,17-diiodo-25,26,27,28-tetrahydroxythiacalix[4]arene, 5,17-dibromo-25,26,27,28-tetrahydroxythiacalix[4]arene, 5,11,17,23-tetra(4-pyridylimino)-25,26,27,28-tetrahydroxythiacalix[4]arene, 5,11,17,23-tetra(phenylethynyl)-25,26,27,28-tetrahydroxythiacalix[4]arene, 5,11,17,23-tetraethynyl-25,26,27,28-tetrahydroxythiacalix[4]arene.

The different conformers of the compounds having formulas (I), (Ia), (Ib) and (Ic), that is, having cone, partial cone, 1,2 alternating, 1,3 alternating conformation (Tetrahedron 1999, 40, 373–376) form an integral part of the invention.

Generally, the thiacalix[4]arenes according to the present invention can be prepared using methods similar to those used, for example, for the synthesis of 25,26,27,28-tetrahydroxythiacalix[4]arene described in particular in Tetrahedron Letters, 1998, 39, 2311–2314, or for the synthesis of du 5,11,17,23-tetra-(tert-butyl)-25,26,27,28-tetrahydroxythiacalix[4]arene, or the compounds according to the invention can be obtained by total or partial functionalization of these known compounds utilized as starting products.

The compounds having formula (I) can comprise precursor groups of other functions that are generated later in one or a plurality of steps.

The compounds having formula (I), in which $R_{1a}$, $R_{2a}$, $R_{3a}$ and/or $R_{4a}$ are different from hydrogen can be obtained using respective compounds, in which said $R_{1a}$, $R_{2a}$, $R_{3a}$ and/or $R_{4a}$ group(s) is a hydrogen atom by total or partial functionalization of the hydroxyl function in the presence of a base by the action, respectively, of a halogen derivative of the type Hal-$R'_{1a}$, Hal-$R'_{2a}$, Hal-$R'_{3a}$ and/or Hal-$R'_{4a}$ in which Hal is a halogen atom, for example an atom of chlorine or iodine and $R'_{1a}$, $R'_{2a}$, $R'_{3a}$ et $R'_{4a}$ are, respectively, $R_{1a}$, $R_{2a}$, $R_{3a}$ or $R_{4a}$ or a precursor group of these latter.

In order to obtain the —$O(C_1$–$C_{12})$alkyl functionalization, one works, for example, in the presence of the number of adapted equivalents of a alkaline metal carbonate base like potassium, cesium or sodium carbonate in reflux acetone.

In order to obtain the —$OSiR_2R_3R_4$, $R_2$, $R_3$, $R_4$ functionalization as defined for (I), one works in the presence of imidazole, for example.

In order to obtain the —$OSO_2$—$R_1$, $R_1$ functionalization as defined for (I), one works, for example, in the presence of an amine type base like triethylamine in reflux toluene.

The compounds (I) in which $R_{1b}$, $R_{2b}$, $R_{3b}$ and/or $R_{4b}$ are a group different from hydrogen are, for example, totally or partially functionalized using corresponding thiacalixarene, in which said $R_{1b}$, $R_{2b}$, $R_{3b}$ and/or $R_{4b}$ group(s) are hydrogen or a precursor group of the desired function.

Details on these functionalization processes are provided in the examples that follow.

The compounds (I) in which $R_{1b}$, $R_{2b}$, $R_{3b}$ and/or $R_{4b}$ are a derivative of the alcynyl type can be synthetized:

either when the alcynyl derivative is of the —C≡C—$R_6$ type, in which $R_6$ is a ($C_1$–$C_4$) alkyl, tri($C_1$–$C_4$) alkylsilyl, phenyl group or a group having the formula:

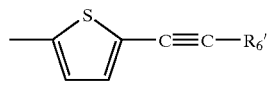

where $R_6'$ is such as hereinbefore defined for (I) using the respective compound (I), in which said $R_{1b}$, $R_{2b}$, $R_{3b}$, and/or $R_{4b}$ group(s) are a halogen atom, by the action of the H—C≡C—$R_6$, $R_6$ derivative being such as hereinbefore described in the presence of tri- or diethylamine and a palladium catalyst according to the Sonogashira reaction, as described in Tetrahedron Letters 1975, 50, 4467–4470 or Eur. J. Org. Chem. 2000, 3679–3681, for example;

or when the alcynyl derivative is —C≡C—H, using the respective compound (I), in which the $R_{1b}$, $R_{2b}$, $R_{3b}$ and/or $R_{4b}$ group(s) is a —C≡C—$R_6$ group, with $R_6$ being a tri ($C_1$–$C_4$) alkylsilyl, by the action of potassium fluoride according to Chem. Commun. 2000, 1513–1514.

The method described by Z.-T. Huang et al in Synthetic Communications, 1997, 27(21), 3763–3767, for the synthesis of p-nitrocalixarenes by nitration of the corresponding calixarenes is carried out by the action of potassium nitrate and aluminum trichloride in acetonitrile at 0° C. These operational conditions do not allow the synthesis of compounds (I) according to the invention, in which said $R_{1b}$, $R_{2b}$, $R_{3b}$ and/or $R_{4b}$ are a nitro group.

The action of nitrogen dioxide or dinitrogen tetroxide in the presence of an etherized solvent been shown unexpectedly to make possible synthesis of compounds having formula (I) comprising a nitro function.

Also, the object of the present invention is a method for preparation of the compounds of formula (I), in which one at least of the $R_{1b}$, $R_{2b}$, $R_{3b}$ or $R_{4b}$ substituents is a nitro, —N=CHR$_5$, or —NR$_7$R$_8$, in which $R_7$ is a hydrogen atom $R_8$ is a hydrogen atom or a —C(O)R$_5$ with $R_5$ chosen from the group comprising a ($C_1$–$C_4$) alkyl, pyridyl or phenyl group characterized in that:

a) if $R_{1b}$, $R_{2b}$, $R_{3b}$ and/or $R_{4b}$ being a nitro group, the compound (I) is obtained by nitration of the corresponding thiacalix[4]arene, in which said $R_{1b}$, $R_{2b}$, $R_{3b}$ and/or $R_{4b}$ being a hydrogen atom, by the action of the nitrogen dioxide or the dinitrogen tetroxide in the presence of an etherize solvent;

b) if $R_{1b}$, $R_{2b}$, $R_{3b}$ and/or $R_{4b}$ is an amino group, the compound (I) is obtained by reduction of the respective compound (I), in which said group(s) $R_{1b}$, $R_{2b}$, $R_{3b}$ and/or $R_{4b}$ is a nitro group;

c) if $R_{1b}$, $R_{2b}$, $R_{3b}$ and/or $R_{4b}$ being —N=CHR$_5$, $R_5$ being a ($C_1$–$C_4$) alkyl, phenyl or pyridyl group, the compound (I) is prepared using the respective compound (I), in which said $R_{1b}$, $R_{2b}$, $R_{3b}$ and/or $R_{4b}$ are an amino group, by the action of an aldehyde $R_5$—CHO or a ketone $R_5$—C(O) $R_9$, $R_5$ and $R_9$, being the same or different, independently being one of the other, a ($C_1$–$C_4$) alkyl, pyridyl or phenyl group;

d) if $R_{1b}$, $R_{2b}$, $R_{3b}$ and/or $R_{4b}$, being a —NHC(O)R$_5$ group, in which $R_5$ is a ($C_1$–$C_4$)alkyl, pyridyl or phenyl group, the compound (I) is obtained using the respective compound (I), in which $R_{1b}$, $R_{2b}$, $R_{3b}$ and/or $R_{4b}$ being an amino group, by the action of the acid halogenide Hal-C(O) $R_5$, in which Hal is a halogen atom and $R_5$ and is as hereinbefore defined.

For the synthesis described in a), dimerized nitrogen dioxide can be used called dinitrogen tetroxide. This nitrogen dioxide forms a complex with the ether used that can be, for example, of the di, tri or tetraglyme or a crown ether. Commercial nitrogen dioxide or prepared on site is used, for example, by the action of a nitrate of the alkaline metal nitrate type, such as potassium nitrate in the presence of a Lewis acid such as aluminum trichloride. The nitrogen dioxide/ether complex can be synthesized in situ or previously prepared by bubbling the nitrogen dioxide in the cooled ether solvent. Reference can be made to the Journal of Molecular Structure, 1988, 178, 135.

For the synthesis described in b), reducer pairs of the tin/hydrochloric acid or zinc/acetic acid type can be used.

For the synthesis described in c), one works preferably in an acid environment, for example in the presence glacial acetic acid according to the method described by Angew Chem. Int. Ed. Engl. 1996, 35(5), 538–540.

For the synthesis described in d) reference can be made to J. Chem. Soc. Perkin Trans. 2, 1996, 1175.

The functional groups eventually present in the compounds having the formula (I), (Ia), (Ib), (Ic) and in the reaction intermediates, can be protected either permanently or temporary by protector group that assure proper synthesis of the expected compounds. The protection or deprotection reactions are carried out according to the methods well known to the specialist in the art. The specialist in the art will be capable of choosing the appropriate protector groups.

The compounds (I) are isolated and purified using classical separation techniques. For example, recrystallizations or even classical chromatographic techniques in chiral or non-chiral phase can be used.

An other object of the present invention is the complexes (II) of compounds of the formula (I), (Ia), (Ib) and (Ic) with a metal and in particular a transition metal at variable degrees of oxidation. The following can be cited as examples of a transition metal: copper, palladium, mercury, gold and more preferably, silver, zinc, platinum or lead.

These complexes (II) are obtained using methods well known to the specialist in the art, for example, by adding a metal salt to the thiacalix[4]arenes having the formula (I) in solution in an appropriate organic solvent, for example tetrahydrofurane, chloroform or pyridine.

The complexes according to the invention are, for example, capable of being obtained by reaction of a thiacalix [4]arenes having the formula (I) with a metal derivative of the type: AgSO$_3$CF$_3$, zinc (II) chloride, copper (II) chloride, Trans-[PtCl(PEt$_3$)$_2$(C≡C-phenyl)] or Trans-{PtCl(PEt$_3$)$_2$ [C≡C-(4-pentylphenyl)]} or another platinum complex comprising another phosphine of the trialkylphosphine type and/or a phenyl group differently substituted in position 4 by another alkyl group, this list not being in any way limiting whatsoever.

The compounds having formula (I) as well as their metal complexes (II) according to the invention have third-order non-linear optical properties.

The optical limitation measurements were done using a measurement bench of the same type as those previously described by: D. Vincent in Nonlinear Optics 1999, 21, 413–422 et D. D. James, K. J. McEwan in Nonlinear Optics, 1999, 21, 377–389. For an incident laser beam of variable energy (0–400 µJ) the maximal transmitted energies were measured varying from 100 µJ to 5 µJ for the compounds providing the best results.

The derivatives according to the invention are thus particularly interesting and can be utilized especially as optical limiters. They can be used for manufacturing materials having optical limiter properties. They can be incorporated into vitreous type matrices by using, for example, the sol-gel (C. J. Brinker, G. W. Scherer, Sol-Gel Science. The Physics and Chemistry of Sol-Gel Processing, Academic Press, 1990 et L. C. Klein, Sol-Gel Optics: Processing and Applications, Kluwer Academic Publishers, 1994) for producing materials for use as protection against lasers.

The complexes (II) according to the invention having zinc, copper or nickel are the colored compounds that have interesting coloration properties as a function of temperature. For example, the compound II.5 (example 5B) goes from the color purple to a Bordeaux red once the temperature reaches 25° C. This transformation is reversible and the compound returns to its initial coloration upon cooling. The compound is stable over time and can sustain a great many cycles of color change. This was the object of a study using differential calorimetric analysis (DSC820 Mettler Toledo), which demonstrated a phase transition peak of between 25 and 40° C. corresponding to the color change phenomenon described.

Accordingly, they can be used for manufacturing thermochrome materials.

The thiacalix[4]arenes (1) according to the invention can be used for water treatment, they especially make possible selective extraction of organic compounds (Chemistry Letters, 1999, 777) or cations (Tetrahedron Letters 1998, 39, 7559 and 2001, 42, 1021).

Similarly, certain thiacalix[4]arenes (I) and their metal complexes (II), in virtue of their second-order non-linear optical properties, can be used as frequency doublers (Angew Chem. Int. Ed. Engl, 1992, 31(8), 1075).

The examples that follow illustrate the invention without limiting it.

The nuclear magnetic resonance (NMR) spectra were done at 300 MHz and at 25° C. and the chemical shifts are expressed in ppm. The following abbreviations are used: s=singlet, m=multiplet, d=doublet, t=triplet, sex=sextuplet.

EXAMPLES

A—Thiacalix[4]arenes (I)

Example 1A 5,11,17,23-Tetraiodo-25,26,27,28-tetrahydroxythiacalix[4]arene, Compound I.1

1 g of 25,26,27,28-tetrahydroxythiacalix[4]arene (prepared according to Tetrahedron Letters, 1998, 39, 2311–2314) is dissolved in 60 ml of dichloromethane. 2.979 g of benzyltrimethyl ammonium dichloroiodate are added to this solution. The orange suspension is stirred for 30 minutes and then 30 ml of methanol are added; it is then stirred for another 30 minutes and treated with 1.62 g of calcium carbonate. The suspension is stirred for 24 hours at room temperature. After addition of 6 ml of concentrated hydrochloric acid and 100 ml of methanol, the suspension is decolorized using 160 ml of an aqueous solution of 10% sodium hydrogen sulfate, then filtered. The residue is washed with approximately 16 ml 1M hydrochloric acid, 90 ml of water, 10 ml of methanol and 50 ml of dichloromethane to produce a white solid (65% yield).

RMN$^1$H (δ, ppm, $C_5D_5N$): 7.83 (s, 8H).

Example 2A 5,11,17,23-Tetrabromo-25,26,27,28-tetrahydroxythiacalix[4]arene, Compound I.2

1 g of 25,26,27,28-tetrahydroxythiacalix[4]arene is suspended in 50 ml of acetone. 1.43 g of N-bromosuccinimide are added to this suspension. The reaction mixture is mixed under nitrogen, protected from light and at room temperature for 24 hours. The solvents are evaporated, then the solid obtained is washed with approximately 50 ml of water, 20 ml of methanol and 20 ml of dichloromethane. The light brown residue obtained is collected in 10 ml of pyridine and then precipitated using acetonitrile in order to obtain a white powder (60% yield).

2-butanone can be used in lieu of acetone as the solvent.

RMN$^1$H (δ, ppm, $C_5D_5N$): 7.83 (s, 8H); 12.34 (s, 4H).

Example 3A 5,11,17,23-Tetra(tert-butyl)-25-propoxy-26,27,28-trihydroxythiacalix[4]arene, Compound I.3

30 g of 5,11,17,23-tetra(tert-butyl)-25,26,27,28-tetrahydroxythiacalix[4]arene (prepared according to Tetrahedron Letters, 1997, 38(22), 3972–3972) are suspended in 20 ml of acetone and 0.191 g of potassium hydrogen carbonate are added. The suspension is reflux mixed under inert atmosphere for approximately 30 minutes and then 0.16 ml of n-propyl iodide are added. The suspension is reflux stirred for approximately 24 hours; then the solvents are evaporated. The residue is collected in 90 ml of dichloromethane and acidified using 30 ml of 1M hydrochloric acid. The organic phase is washed using 30 ml of saturated sodium chloride solution and twice with 30 ml of water and then dried over sodium sulfate. The organic phase is concentrated and then precipitated using methanol. The yellow powder obtained is recrystallized in a chloroform/methanol mixture in order to produce colorless crystals (60% yield).

RMN$^1$H (δ, ppm, $CDCl_3$): 0.80 (s, 9H); 1.16 (t, 3H); 1.22 (s, 9H); 1.34 (s, 18H); 2.06 (sex, 2H); 4.45 (t, 2H); 6.96 (s, 2H); 7.66 and 7.64 (s, 4H); 7.97 (s, 2H).

Example 4A 5,11,17,23-Tetra(tert-butyl)-25,27-di(tert-butyldimethylsiloxy)-26,28-dihydroxythiacalix[4]arene, Compound I.4

0.5 g de 5,11,17,23-tetra(tert-butyl)-25,26,27,28-tetrahydroxythiacalix[4]arene are dissolved in 40 ml of dichloromethane. 0.1 g of imidazole and 1.255 g chloride of tert-butyldimethylsilane are added to the solution. The solution is stirred for approximately 24 hours at room temperature and then acidified using 40 ml of 1M hydrochloric acid. The organic phase is washed using 30 ml of saturated sodium chloride solution and twice with 30 ml of water and then dried over sodium sulfate. The organic phase is concentrated and then precipitated using methanol. The product obtained can then be recrystallized in a chloroform/methanol mixture in order to provide a white powder (90% yield).

RMN$^1$H (δ, ppm, $CDCl_3$): 0.33 (s, 12H); 0.85 (s, 18H); 1.19 (s, 18H); 1.31 (s, 18H); 7.06 (s, 4H); 7.62 (s, 4H).

Example 5A

5,11,17,23-Tetra(tert-butyl)-25,26,27,28-tetrahexyloxythiacalix[4]arene, Compound I.5

0.73 g of 5,11,17,23-tetra(tert-butyl)-25,26,27,28-tetrahydroxythiacalix[4] are suspended in 50 ml of acetone. 2.768 g potassium carbonate are added to the mixture that is heated to reflux and under inert atmosphere until clarification. 3 ml of 1-iodohexane are added. The mixture is heated to reflux for approximately 24 hours. The solvents are evaporated under reduced pressure then the residue obtained is collected in 50 ml of chloroform. This organic phase is then washed with approximately 40 ml of 1M hydrochloric acid, 40 ml of saturated sodium chloride solution and 2 times with 40 ml of water. The organic phase is dried over sodium sulfate and then the solvents are evaporated under reduced pressure. The crude powder is recrystallized in a chloroform/methanol mixture in order to produce a white powder (65% yield).

RMN$^1$H ($\delta$, ppm, CDCl$_3$): 0.85 (t, 12H); 0.99 to 1.14 (m, 32H); 1.27 (s, 36H); 3.81 (t, 8H); 7.30 (s, 8H).

Example 6A

5,11,17,23-Tetrakis(phenylazo)-25,26,27,28-tetrahydroxythiacalix[4]arene, Compound I.6 a) Tetrafluoroborate of Benzene Diazonium 4.55 ml of aniline are added to 12.6 ml of concentrated hydrochloric acid and 3.65 g of sodium nitrite at a temperature of 0° C. A solution of 7.6 g of sodium tetrafluoroborate in 15 ml of water is added. The white precipitate formed is filtered, then washed with 5 ml of iced water, 3 ml of ethanol and 5 ml of diethyl ether. The product is then dried on filter paper for 13 hours (yield 70%).

b) 0.5 g of 25,26,27,28-tetrahydroxythiacalix[4]arene and 1.6 g of benzene diazonium tetrafluoroborate are dissolved in 20 ml of tetrahydrofurane. 1 ml of pyridine is added at 0° C. to and the reaction mixture is stirred for 16 hours at room temperature, then 50 ml of methanol are added in order to obtain a yellow precipitate. The precipitate obtained is washed, successively, in methanol and diethyl ether and recrystallized in a pyridine methanol mixture (64% yield).

RMN$^1$H ($\delta$, ppm, C$_5$D$_5$N): 7.32 (t, 4H); 7.41 (t, 8H); 7.90 (d, 8H); 8.54 (s, 8H); 14.6 (s, 4H).

Example 7A

5,11,17,23-Tetrakis(4-nitrophenylazo)-25,26,27,28-tetrahydroxythiacalix[4]arene, Compound I.7 a) Tetrafluoroborate of 4-nitrobenzene diazonium 17 g or 4-nitroaniline are dissolved heated in 65 ml of 6M hydrochloric acid. After cooling the mixture to 0° C., 9 g or sodium nitrite, then 20 g of sodium tetrafluoroborate are added. The precipitate is filtered and added successively with an aqueous solution of 5% sodium tetrafluoroborate, ethanol and diethyl ether. Finally, the product is dried on filter paper (97% yield).

b) 0.35 g of 25,26,27,28-tetrahydroxythiacalix[4]arene and 1.4 g of 4-nitrobenzene diazonium tetrafluoroborate are dissolved in 20 ml of tetrahydrofurane. 1 ml of pyridine is added at 0° C. The reaction mixture becomes orange and a light precipitate appears. After two days, the precipitate is filtered and washed successively with cold tetrahydrofurane and methanol. The precipitate obtained is recrystallized in the pyridine in order to produce red crystals.

RMN$^1$H ($\delta$, ppm, C$_5$D$_5$N): 8.17 (s, 4H); 8.29 and 7.86 (2d, 2×8H); 8.60 (s, 8H).

Example 8A

5,11,17,23-Tetra(tert-butyl)-25,27-di(4-toluenesulfonyloxy)-26,28-dihydroxythiacalix[4]arene, Compound I.8

0.5 g of 5,11,17,23-tetra(tert-butyl)-25,26,27,28-tetrahydroxythiacalix[4]arene are dissolved in 20 ml of toluene in reflux under nitrogen atmosphere. 0.926 g of 4-toluene sulfonyl chloride and 1.5 ml of triethylamine are added to the reaction mixture. The reaction mixture is reflux heated for 6 hours then slowly cooled to room temperature. The solvents are evaporated and the brown residue obtained is collected with 40 ml of dichloromethane, washed three times with 30 ml 1N hydrochloric acid and four times with 30 ml of water, then dried over sodium sulfate. After filtration, evaporation of the solvents and addition of methanol, a white powder precipitates. The powder obtained is recrystallized in a dichloromethane/methanol mixture. (73% yield).

RMN$^1$H ($\delta$, ppm, CDCl$_3$): 1.29 and 0.84 (s, 36H); 2.49 (s, 6H); 7.01 (s, 4H); 7.60 (s, 4H); 7.86 and 7.36 (d, 8H);

Example 9A

5,11,17,23-Tetranitro-25,26,27,28-tetrahydroxythiacalix[4]arene, Compound I.9

0.6 g of 25,26,27,28-tetrahydroxythiacalix[4]arene are suspended in 20 ml of diethylene glycol dimethyl ether (diglyme), 0.9 g of potassium nitrate and 3.16 g of aluminum trichloride are added to the suspension. The reaction is gently activated by heating until the appearance of a brown color, then stirred for 12 hours at room temperature. The suspension is hydrolyzed with 90 ml of water. The organic phase is extracted with 2 times 30 ml of ethyl acetate. The 2 organic fractions are combined and then dried over sodium sulfate. The solvents are evaporated under reduced pressure, then a precipitate is obtained using approximately 50 ml of diethyl ether. The powder obtained is purified by chromatography over a silica gel column by eluating with a chloroform/methanol mixture, 7/3 (v/v) in order to produce a yellow solid (35% yield).

RMN$^1$H ($\delta$, ppm, CD$_3$CN): 8.44 (s, 4H).

Example 10A

Tetrachlorhydrate of 5,11,17,23-tetramino-25,26,27,28-tetrahydroxythiacalix[4]arene, Compound I.10

0.5 g of compound I.9 is suspended in 20 ml of concentrated hydrochloric acid. 2 g of metallic tin are added to this suspension. The reaction mixture is reflux heated for 1 hour. The white suspension is cooled in an ice bath and then filtered. The white precipitate is washed with cold hydrochloric acid and then with diethyl ether (quantitative yield).

RMN$^1$H ($\delta$, ppm, (CD$_3$)$_2$SO): 7.44 (s, 8H); 9.92 (s, 4H).

Example 11A

25,27-Di(4-toluenesulfonyloxy)-26,28-dihydroxythiacalix[4]arene, Compound I.11

Prepared according to operational method described in EXAMPLE 8A, using 25,26,27,28-tetrahydroxythiacalix[4]arene.

Example 12A

25,27-Di(tert-butyldimethylsiloxy)-26,28-dihydroxythiacalix[4]arene, Compound I.12

Prepared according to the same operational method described in EXAMPLE 4A, using 25,26,27,28-tetrahydroxythiacalix[4]arene.

RMN$^1$H ($\delta$, ppm, CDCl$_3$): 0.33 (s, 12H); 1.15 (s, 18H); 6.07 (d, 4H); 6.43 (t, 2H); 6.79 (t, 2H); 7.60 (d, 4H)

Example 13A

5,11,17,23-Tetrakis(phenylazo)-25,27-di(4-toluenesulfonyloxy)-26,28-dihydroxythiacalix[4]arene, Compound I.13

Prepared according to the operational method described in EXAMPLE 8A, using compound I.6.

Example 14A

5,11,17,23-Tetrakis(4-nitrophenylazo)-25,27-di(4-toluenesulfonyloxy)-26,28-dihydroxythiacalix[4]arene, Compound I.14

Prepared according to the operational method described in EXAMPLE 8A, using compound I.7.

Example 15A

5,17-Diiodo-25,26,27,28-tetrahydroxythiacalix[4]arene, Compound I.15

Prepared by forming the intermediate 5,17-diiodo-25,27-di(tert-butyldimethylsiloxy)-26,28-dihydroxythiacalix[4]arene according to the operational method described in EXAMPLE 1A using compound I.12 and 2.1 equivalents of benzyl trimethyl ammonium dichloroiodate, which is then treated with potassium fluoride in the presence of crown ether (18-crown-6) (G. Stork, P. F. Hudrlik, J. Am. Chem. Soc., 60, 4462, 1968; C. L. Liotta, P. H. Harris, J. Am. Chem. Soc., 96, 2250, 1974) or with tetrabutyl ammonium fluoride in tetrahydrofurane (E. J. Corey, A. Venkateswarlu, J. Am. Chem. Soc, 94, 6190, 1972).

Example 16A

5,17-Dibromo-25,26,27,28-tetrahydroxythiacalix[4]arene, Compound I.16

Prepared according to the operational method described in EXAMPLE 15A, using 2.1 equivalents of N-bromosuccinimide.

The EXAMPLES according to the invention are presented in TABLE 1, below.

TABLE 1

(I)

[Structure of thiacalix[4]arene with substituents OR$_{1a}$, OR$_{2a}$, OR$_{3a}$, OR$_{4a}$ on upper rim and R$_{1b}$, R$_{2b}$, R$_{3b}$, R$_{4b}$ on lower rim, linked by S bridges]

| EXAMPLES | R$_{1a}$ | R$_{3a}$ | R$_{2a}$ | R$_{4a}$ | R$_{1b}$ | R$_{3b}$ | R$_{2b}$ | R$_{4b}$ |
|---|---|---|---|---|---|---|---|---|
| 1A | R$_{1a}$ = R$_{2a}$ = R$_{3a}$ = R$_{4a}$ = H | | | | R$_{1b}$ = R$_{2b}$ = R$_{3b}$ = R$_{4b}$ = I | | | |
| 2A | R$_{1a}$ = R$_{2a}$ = R$_{3a}$ = R$_{4a}$ = H | | | | R$_{1b}$ = R$_{2b}$ = R$_{3b}$ = R$_{4b}$ = Br | | | |
| 3A | —(CH$_2$)$_2$CH$_3$ | | R$_{2a}$ = R$_{3a}$ = R$_{4a}$ = H | | R$_{1b}$ = R$_{2b}$ = R$_{3b}$ = R$_{4b}$ = —C(CH$_3$)$_3$ | | | |
| 4A | R$_{1a}$ = R$_{3a}$ = —Si(CH$_3$)$_2$[C(CH$_3$)$_3$] | | R$_{2a}$ = R$_{4a}$ = H | | R$_{1b}$ = R$_{2b}$ = R$_{3b}$ = R$_{4b}$ = —C(CH$_3$)$_3$ | | | |
| 5A | R$_{1a}$ = R$_{2a}$ = R$_{3a}$ = R$_{4a}$ = —(CH$_2$)$_5$CH$_3$ | | | | R$_{1b}$ = R$_{2b}$ = R$_{3b}$ = R$_{4b}$ = —C(CH$_3$)$_3$ | | | |
| 6A | R$_{1a}$ = R$_{2a}$ = R$_{3a}$ = R$_{4a}$ = H | | | | R$_{1b}$ = R$_{2b}$ = R$_{3b}$ = R$_{4b}$ = 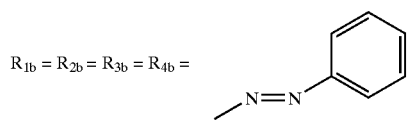 | | | |
| 7A | R$_{1a}$ = R$_{2a}$ = R$_{3a}$ = R$_{4a}$ = H | | | | R$_{1b}$ = R$_{2b}$ = R$_{3b}$ = R$_{4b}$ = 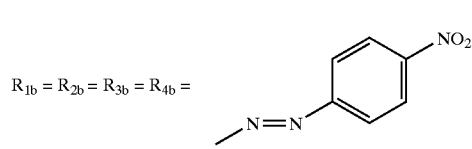 | | | |
| 8A | R$_{1a}$ = R$_{3a}$ = 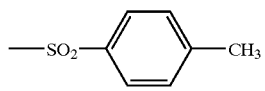 | | R$_{2a}$ = R$_{4a}$ = H | | R$_{1b}$ = R$_{2b}$ = R$_{3b}$ = R$_{4b}$ = —C(CH$_3$)$_3$ | | | |

TABLE 1-continued

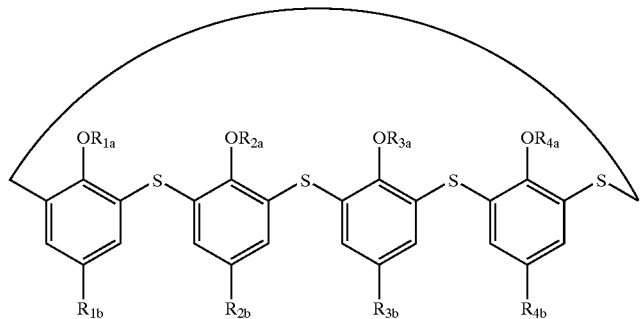

| EXAMPLES | $R_{1a}$ | $R_{3a}$ | $R_{2a}$ | $R_{4a}$ | $R_{1b}$ | $R_{3b}$ | $R_{2b}$ | $R_{4b}$ |
|---|---|---|---|---|---|---|---|---|
| 9A | $R_{1a} = R_{2a} = R_{3a} = R_{4a} = H$ | | | | $R_{1b} = R_{2b} = R_{3b} = R_{4b} = -NO_2$ | | | |
| 10A | $R_{1a} = R_{2a} = R_{3a} = R_{4a} = H$ | | | | $R_{1b} = R_{2b} = R_{3b} = R_{4b} = -NH_3^+, Cl^-$ | | | |
| 11A | $R_{1a} = R_{3a} = -SO_2-C_6H_4-CH_3$ | | $R_{2a} = R_{4a} = H$ | | $R_{1b} = R_{2b} = R_{3b} = R_{4b} = H$ | | | |
| 12A | $R_{1a} = R_{3a} = -Si(CH_3)_2[C(CH_3)_3]$ | | $R_{2a} = R_{4a} = H$ | | $R_{1b} = R_{2b} = R_{3b} = R_{4b} = H$ | | | |
| 13A | $R_{1a} = R_{3a} = -SO_2-C_6H_4-CH_3$ | | $R_{2a} = R_{4a} = H$ | | $R_{1b} = R_{2b} = R_{3b} = R_{4b} = -N=N-C_6H_5$ | | | |
| 14A | $R_{1a} = R_{3a} = -SO_2-C_6H_4-CH_3$ | | $R_{2a} = R_{4a} = H$ | | $R_{1b} = R_{2b} = R_{3b} = R_{4b} = -N=N-C_6H_4-NO_2$ | | | |
| 15A | $R_{1a} = R_{2a} = R_{3a} = R_{4a} = H$ | | | | $R_{1b} = R_{3b} = I$ | | $R_{2b} = R_{4b} = H$ | |
| 16A | $R_{1a} = R_{2a} = R_{3a} = R_{4a} = H$ | | | | $R_{1b} = R_{3b} = Br$ | | $R_{2b} = R_{4b} = H$ | |
| 17A | $R_{1a} = R_{2a} = R_{3a} = R_{4a} = H$ | | | | $R_{1b} = R_{2b} = R_{3b} = R_{4b} = -N=C(H)-(4-pyridyl)$ | | | |
| 18A | $R_{1a} = R_{2a} = R_{3a} = R_{4a} = H$ | | | | $R_{1b} = R_{2b} = R_{3b} = R_{4b} = -NH-C(O)-C_6H_5$ | | | |
| 19A | $R_{1a} = R_{2a} = R_{3a} = R_{4a} = $ n-propyl | | | | $R_{1b} = R_{2b} = R_{3b} = R_{4b} = Br$ | | | |
| 20A | $R_{1a} = R_{2a} = R_{3a} = R_{4a} = $ n-propyl | | | | $R_{1b} = R_{2b} = R_{3b} = R_{4b} = I$ | | | |
| 21A | $R_{1a} = R_{2a} = R_{3a} = R_{4a} = $ n-propyl | | | | $R_{1b} = R_{2b} = R_{3b} = R_{4b} = -C{\equiv}C-Si(CH_3)_3$ | | | |
| 22A | $R_{1a} = R_{2a} = R_{3a} = R_{4a} = $ n-propyl | | | | $R_{1b} = R_{2b} = R_{3b} = R_{4b} = -C{\equiv}C-H$ | | | |

TABLE 1-continued

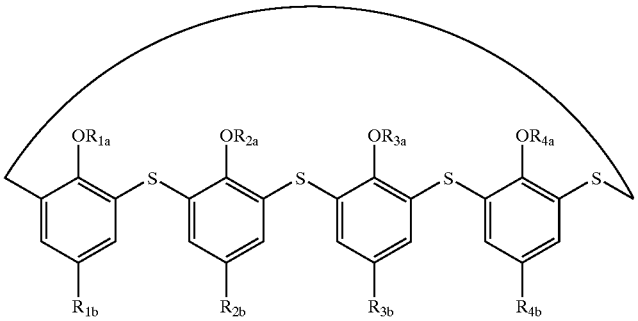

(I)

| EXAMPLES | $R_{1a}$ | $R_{3a}$ | $R_{2a}$ | $R_{4a}$ | $R_{1b}$ | $R_{3b}$ | $R_{2b}$ | $R_{4b}$ |
|---|---|---|---|---|---|---|---|---|
| 23A | $R_{1a} = R_{2a} = R_{3a} = R_{4a}$ = n-propyl | | | | $R_{1b} = R_{2b} = R_{3b} = R_{4b}$ = 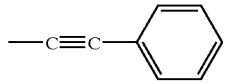 | | | |
| 24A | $R_{1a} = R_{2a} = R_{3a} = R_{4a}$ = n-propyl | | | | $R_{1b} = R_{2b} = R_{3b} = R_{4b}$ = 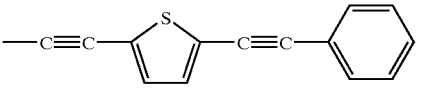 | | | |
| 25A | $R_{1a} = R_{2a} = R_{3a} = R_{4a}$ = n-propyl | | | | $R_{1b} = R_{2b} = R_{3b} = R_{4b}$ = 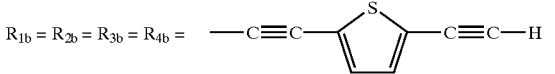 | | | |
| 26A | $R_{1a} = R_{2a} = R_{3a} = R_{4a}$ = H | | | | $R_{1b} = R_{2b} = R_{3b} = R_{4b}$ = —C≡C—H | | | |
| 27A | $R_{1a} = R_{2a} = R_{3a} = R_{4a}$ = H | | | | $R_{1b} = R_{2b} = R_{3b} = R_{4b}$ = 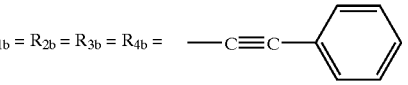 | | | |

Example 19A 5,11,17,23-Tetrabromo-25,26,27,28-tetrapropoxythiacalix[4]arene Compound I.19

1 g of 5,11,17,23-tetrabromo-25,26,27,28-tetrahydroxythiacalix[4]arene (compound I.2) is suspended in 60 ml of acetone. 3.2 g of cesium carbonate are added to this suspension. The mixture is reflux heated under nitrogen until clearing and then 1.2 ml of 1-iodopropane are added. The mixture is heated to reflux for approximately 24 hours. The solvents are evaporated under reduced pressure; then the residue obtained is collected in 90 ml of chloroform. The organic phase is then washed with approximately 40 ml of 1M hydrochloric acid and 2×40 ml of water. The organic phase is dried over sodium sulfate and then the solvents are evaporated under reduced pressure. The crude powder is purified by chromatography over silica (silica, 2 CHCl$_3$/8 hexane)-80% yield.

Example 20A 5,11,17,23-tetraiodo-25,26,27,28-tetrapropoxythiacalix[4]arene(2), Compound I.20

1 g of 5,11,17,23-tetraiodo-25,26,27,28-tetrahydroxythiacalix[4]arene (compound I.1) is suspended in 60 ml of acetone. 2.6 g of cesium carbonate are added to this suspension. The mixture is reflux heated under nitrogen until clearing and then 1 ml of 1-iodopropane are added. The mixture is reflux heated for approximately 24 hours. The solvents are evaporated under reduced pressure; then the residue obtained is collected in 90 ml of chloroform. The organic phase is then washed with approximately 40 ml of 1M hydrochloric acid and 2×40 ml of water. The organic phase is dried over sodium sulfate and then the solvents are evaporated under reduced pressure. The crude powder is purified by chromatography over silica (silica, 2 chloroform/8 hexane)-75% yield.

Example 21A

5,11,17,23-tetratrimethylsilylethynyl-25,26,27,28-tetrapropoxythiacalix[4]arene (3), Compound I.21

Approach 1:

0.5 g of 5,11,17,23-tetraiodo-25,26,27,28-tetrapropoxythiacalix[4]arene (compound I.20) are suspended in 20 ml of deoxygenated triethylamine. 30 mg of dichloro-bis-triphenyl phosphine palladium (II), 4 mg of cupreous iodide and 0.2 g of trimethylsilyl acetylene are added to this suspension. The reaction mixture is heated to 40° C. for 24 hours, then treated with HCl (10%) and extracted using 40 ml of ethyl acetate.

The organic phase is washed with water (2×30 ml) then dried over $Na_2SO_4$. Finally, the product is purified by chromatography over a column (silica 8 hexane/2 chloroform)-75% yield.

Approach 2:

0.5 g of 5,11,17,23-tetrabromo-25,26,27,28-tetrapropoxythiacalix[4]arene (compound I.19) is suspended in 20 ml of deoxygenated triethylamine. 30 mg of dichloro-bis-triphenyl phosphine palladium (II), 5 mg of cupreous iodide and 0.25 g of trimethylsilyl acetylene are added to this suspension. The reaction mixture is heated to 40° C. for 24 hours, then treated with HCl (10%) and extracted using 40 ml of ethyl acetate.

The organic phase is washed with water (2×30 ml) then dried over $Na_2SO_4$. Finally, the product is purified by chromatography over a column (silica 8 hexane/2 chloroform)-70% yield.

Example 22A

5,11,17,23-Tetraethynyl-25,26,27,28-tetrapropoxythiacalix[4]arene, Compound I.22

0.5 g of 5,11,17,23-tetratrimethylsilylethynyl-25,26,27,28-tetrapropoxythiacalix[4]arene (compound I.21) is dissolved in 20 ml of tetrahydrofurane. 1.2 g of fluoride of tetrabutyl ammonium trihydrate are added. The solution is stirred for 2 h under inert atmosphere, then evaporated to dryness. The residue is collected in chloroform. The organic phase is washed with HCl.

1 M, then $H_2O$ and dried over $Na_2SO_4$. After evaporation of the solvents, the product is purified by chromatography over a column (silica, 8 hexane/2 chloroform)-90% yield.

Compose 23A

5,11,17,23-Tetraphenylethynyl-25,26,27,28-tetrapropoxythiacalix[4]arene, Compound I.23

0.5 g of 5,11,17,23-tetraiodo-25,26,27,28-tetrapropoxythiacalix[4]arene is suspended in 20 ml of triethylamine in the absence of oxygen. 20 mg of dichloro-bis-triphenyl phosphine palladium (II), 4 mg of cupreous iodide and 0.2 g of phenyl acetylene are added to this suspension. The reaction mixture is heated to 40° C. for 24 hours, then treated with HCl (10%) and extracted using 40 ml of ethyl acetate; the organic phase is washed with water (2×30 ml) then dried over $Na_2SO_9$. Finally, the product is purified by chromatography over a column (silica 8 hexane/2 chloroform).

Example 24A

Compound I.24

0.24 g or 2-iodo-5-(phenylethynyl) thiophene are suspended in 20 ml of triethylamine in the absence of oxygen. 30 mg of dichloro-bis-phenyl phosphine palladium (II), 0.004 g of cupreous iodide and 0.125 g of 5,11,17,23-tetraethynyl-25,26,27,28-tetrapropoxythiacalix[4]arene (compound I.22). The reaction mixture is heated to 40° C. for 24 hours, then treated with HCl (10%) and extracted using 40 ml of ethyl acetate; the organic phase is washed with water (2×30 ml) then dried over $Na_2SO_4$. Finally, the product is purified by chromatography over a column (8 hexane/2 $CHCl_3$).

A similar compound is also prepared using compound I 22 and 2-iodo-5 [(4-pentylphenyl)ethynyl]thiophene.

B—Complexes (II)

Examples 1B

Complex of Compound I.6 with $AgSO_3CF_3$: $Ag_4$[I.6]$^{4+}$ Compound II.1

0.1 g of compound I.6 is dissolved in 10 ml of chloroform. 0.1 g of $AgSO_3CF_3$ are added to the solution and then the reaction mixture is stirred for approximately 12 hours at room temperature and away from light. After filtration, the red powder obtained is washed with methanol and diethyl ether.

Elementary Microanalysis $Ag_4$[I.6]$(SO_3CF_3)_4$, $C_5H_5N$; Found: C, 34.07%; N, 6.20%; H, 1.82%; S, 12.49%; Ag, 22.41%. Calculated: C, 33.98%; N, 6.24%; H, 1.83%; S, 12.68%; Ag, 21.37%.

Example 2B

Complex of Compound I.6 with $ZnCl_2$: $Zn$[I.6]$_2^{2+}$ Compound II.2

0.1 g of compound I.6 is dissolved in a chloroform/tetrahydrofurane 10/1 (v/v) mixture. 0.1 g of zinc (II) chloride and 0.2 ml of pyridine are added to this orange-colored solution. The solution is stirred for 48 hours at room temperature. The yellow suspension is filtered. The yellow powder obtained is washed with water, methanol and diethyl ether.

Elementary Microanalysis $Zn$[I.6]$_2Cl_2,C_5H_5N$; Found: C, 57.06%; N, 11.29%; H, 3.39%; S, 11.94%; Zn, 3.57%. Calculated: C, 60.00%; N, 11.89%; H, 3.49%; S, 12.00%; Zn, 3.08%.

Example 3B

Complex of Compound I.6 with $CuCl_2$: $Cu_4$[I.6]$^{4+}$ Compound II.3

0.1 g of compound I.6 is dissolved in 10 ml of chloroform. 0.063 g of copper (II) chloride are added to this solution. The suspension is stirred for 24 hours at room temperature. The suspension is filtered, then the solvents are evaporated. The brown colored powder is washed in methanol, in water and in diethyl ether.

Elementary Microanalysis $Cu_4$[I.6]$Cl_8,C_5H_5N$; Found: C, 43.87%; N, 7.86%; H, 2.90%; S, 8.71%; Cu, 16.77%. Calculated: C, 41.50%; N, 8.20%; H, 2.41%; S, 8.36%; Cu, 16.61%.

Example 4B

Complex of Compound I.7 with $AgSO_3CF_3$: $Ag_5$[I.7]$_2^{5+}$ Compound II.4

0.15 g of compound I.7 is dissolved in 20 ml of pyridine. 0.1 g of $AgSO_3CF_3$ are added and then the reaction mixture is stirred for approximately 24 hours at room temperature and away from light. It is precipitated with methanol; the violet powder obtained is washed in methanol and in diethyl ether.

Elementary Microanalysis Ag$_5$[I.7]$_2$(SO$_3$CF$_3$)$_5$, 13C$_5$H$_5$N; Found: C, 46.07%; N, 12.62%; H, 2.38%; S, 9.22%; Ag, 12.14%. Calculated: C, 44.30%; N, 11.52%; H, 2.69%; S, 9.25%; Ag, 11.99%.

Example 5B

Complex of Compound I.7 with ZnCl$_2$: Zn[I.7]$_2$$^{+2}$ Compound II.5

0.1 g of compound I.7 is suspended in 10 ml of tetrahydrofurane. 0.1 g of zinc (II) chloride and 0.9 ml of water are added to this suspension. The suspension is stirred for 69 hours at room temperature. The suspension is filtered. The filtrate is concentrated and then precipitated with methanol. The purple powder obtained is washed in methanol, in water and in diethyl ether.

Elementary Microanalysis Zn[I.7]$_2$Cl$_2$; Found: C, 48.09%; N, 12.63%; H, 2.68%; S, 9.14%; Zn, 3.29%. Calculated: C, 49.60%; N, 14.47%; H, 2.41%; S, 11.00%; Zn, 2.81%.

The deviations obtained among the calculated and experimental results of the elementary analysis are attributable to the presence of solvatation molecule.

Example 6B

Complexes of Platinum with Compound I.22: Compound II.6 Having the Formula:

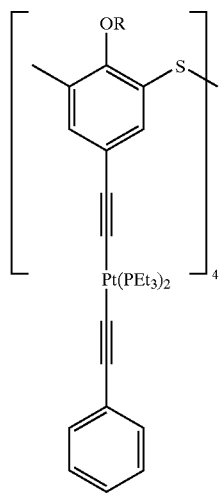

where R=n-propyl 0.1 g of trans-[PtCl(PEt$_3$)$_2$(C≡C-phenyl)] is dissolved in a 1 toluene/1 diethylamine mixture. 0.0003 g of cupreous chloride and then a solution of 0.028 g of 5,11,17,23-tetraethynyl-25,26,27,28-tetrapropoxythiacalix[4]arene (compound 22.1) in 10 ml of toluene are added to this solution. The reaction mixture is stirred at room temperature for 24 hours, evaporated to dryness and collected in dichloromethane. The organic phase is dried on magnesium sulfate and then evaporated to dryness. The residue is purified by chromatography over basic alumina. A complex analogous to compound II.6 using trans-{PtCl(PEt$_3$)$_2$[C≡C-(4-pentylphenyl)]} was also prepared using the same operational method.

Complexes analogous to compound II.6, in which R=methyl or —C$_2$H$_4$O$_2$CNHC$_2$H$_4$Si(OEt)$_3$, were also prepared using the same operational method.

Example 7B

Complexes of Platinum with Compound I.25: Compound II.7 Having the Formula:

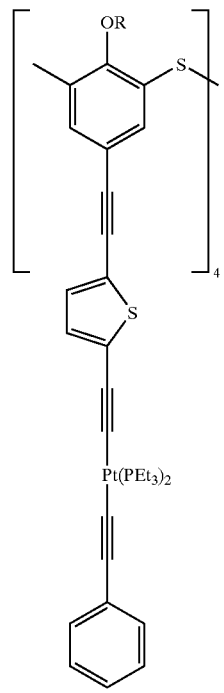

where R = n-propyl

This complex is prepared using the same operating method as that of EXAMPLE 6B. A complex analogous to compound II.7 using trans-{PtCl(PEt$_3$)$_2$[C≡C-(4-pentylphenyl)]} was also prepared using the same operational method.

Complexes analogous to compound II.7, in which R=methyl or —C$_2$H$_4$O$_2$CNHC$_2$H$_4$Si(OEt)$_3$, were also prepared using the same operational method.

What is claimed is:

1. A metal (II) complex with a thiacalix[4]arene, and salts, solvates and hydrates thereof, having the formula (I):

(I)

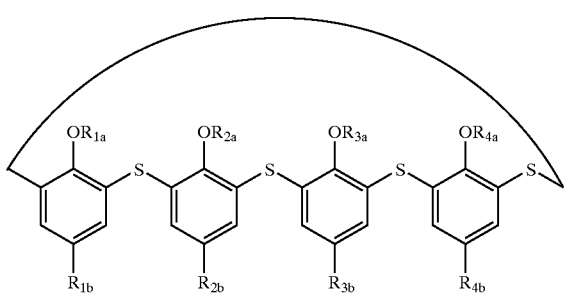

wherein:
(a)—R$_{1a}$, R$_{2a}$, R$_{3a}$ et R$_{4a}$, being the same or different, each is independently:
a hydrogen atom;
a (C$_1$–C$_{12}$) alkyl group;
or a (C$_2$–C$_{12}$) alkenyl group;
R$_{1b}$, R$_{2b}$, R$_{3b}$ and R$_{4b}$, being the same or different, each being:

a hydrogen atom;
a halogen atom;
a ($C_1$–$C_6$) alkyl group;
a phenylazo group eventually substituted preferably in position 4 by a nitro group;
a —N═$CHR_5$ group, in which the $R_5$ is a ($C_1$–$C_4$) alkyl, pyridyl or phenyl group;
a —C≡C—$R_6$ group, in which $R_6$ is a hydrogen atom; a ($C_1$–$C_4$) alkyl, tri($C_1$–$C_4$) akylsilyl, or phenyl group;
a nitro group, or
a —$NR_7R_8$ group, in which $R_7$ is a hydrogen atom and $R_8$ is a hydrogen atom or a —$C(O)R_5$ group with $R_5$ being chosen from a ($C_1$–$C_4$) alkyl, pyridyl or phenyl group, at least one of $R_{1b}$, $R_{2b}$, $R_{3b}$ and $R_{4b}$ being said optionally substituted phenylazo group, said —N═$CHR_5$ group, said —C≡C—$R_6$ group or said —$NR_7R_8$ group;
or wherein:
(b)—$R_{1a}$, $R_{2a}$, $R_{3a}$ and $R_{4a}$, being the same or different, each is independently:
a hydrogen atom;
a ($C_1$–$C_{12}$) alkyl group;
or a ($C_1$–$C_{12}$) alkenyl group;
$R_{1b}$, $R_{2b}$, $R_{3b}$ and $R_{4b}$, being the same or different, each being:
a hydrogen atom;
a halogen atom;
a ($C_1$–$C_6$) alkyl group;
a phenylazo group, eventually substituted preferably at position 4 with a nitro group;
a —N═$CHR_5$ group, in which the $R_5$ is a ($C_1$–$C_4$) alkyl, pyridyl or phenyl group;
a —C≡C—$R_6$ group, in which $R_6$ is a hydrogen atom, a ($C_1$–$C_4$) alkyl, tri ($C_1$–$C_4$) alkylsilyl, phenyl group, or a group having the formula:

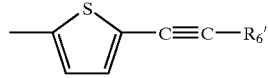

where $R'_6$ is a hydrogen atom or a phenyl, optionally substituted in para by
a ($C_1$–$C_6$) alkyl group;
a nitro group, or
a —$NR_7R_8$ group, in which $R_7$ is a hydrogen atom and $R_8$ is a hydrogen atom or a —$C(O)R_5$ group with $R_5$ being chosen from a ($C_1$–$C_4$) alkyl, pyridyl or phenyl group, at least one of $R_{1b}$, $R_{2b}$, $R_{3b}$ and $R_{4b}$ being said optionally substituted phenylazo group, said —N═$CHR_5$ group, said —C≡C—$R_6$ group or said —$NR_7R_8$ group.

2. A metal (II) complex according to claim 1, part (a), wherein:
$R_{1a}$, $R_{2a}$, $R_{3a}$ and $R_{4a}$, being the same or different, each is independently:
a hydrogen atom;
a ($C_1$–$C_{12}$) alkyl group;
or a ($C_1$–$C_{12}$) alkenyl group,
$R_{1b}$, $R_{2b}$, $R_{3b}$ and $R_{4b}$, being the same or different, each being:
a hydrogen atom;
a halogen atom;
a ($C_1$–$C_6$) alkyl group;
a —N═$CHR_5$ group, in which $R_5$ is a ($C_1$–$C_4$) alkyl, pyridyl or phenyl group;
a —C≡C—$R_6$ group, in which $R_6$ is a hydrogen atom, a ($C_1$–$C_4$) alkyl, tri ($C_1$–$C_4$) alkylsilyl, or phenyl group;
a nitro group, or
a —$NR_7R_8$ group, in which $R_7$ is hydrogen atom and $R_8$ is a hydrogen atom or a group —$C(O)R_5$ with $R_5$ chosen from a ($C_1$–$C_4$) alkyl, pyridyl or phenyl group.

3. A metal (II) complex according to claim 1, part (b), wherein:
$R_{1a}$, $R_{2a}$, $R_{3a}$ and $R_{4a}$, being the same or different, each is independently:
a hydrogen atom;
a ($C_1$–$C_{12}$) alkyl group;
or a ($C_1$–$C_{12}$) alkenyl group,
$R_{1b}$, $R_{2b}$, $R_{3b}$ and $R_{4b}$, being the same or different, each being:
a hydrogen atom;
a halogen atom;
a ($C_1$–$C_6$) alkyl group;
a —N═$CHR_5$ group in which $R_5$ is a ($C_1$–$C_4$) alkyl, pyridyl or phenyl group;
a —C≡C—$R_6$ group, in which $R_6$ is a hydrogen atom; a ($C_1$–$C_4$) alkyl, tri($C_1$–$C_4$)alkylsilyl, phenyl, or a group having the formula:

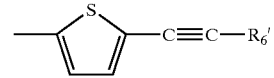

where $R_6'$ is a hydrogen atom or a phenyl, optionally substituted in para by a ($C_1$–$C_6$) alkyl group;
a nitro group, or
a —$NR_7R_8$ group, in which $R_7$ is a hydrogen atom and $R_8$ is a hydrogen atom or a —$C(O)R_5$ group with $R_5$ being chosen from a ($C_1$–$C_4$) alkyl, pyridyl or phenyl group.

4. A metal (II) complex according to claim 1, wherein at least one of the $R_{1b}$, $R_{2b}$, $R_{3b}$ or $R_{4b}$ substituents is a nitro, —N═$CHR_5$ or —$NR_7R_8$ group, wherein $R_7$ is a hydrogen atom and $R_8$ is a hydrogen atom or a —$C(O)R_5$ with $R_5$ being selected from the group consisting of a ($C_1$–$C_4$) alkyl, pyridyl or phenyl group.

5. A metal (II) complex according to claim 1, wherein the thiacalix[4]arene is of formula (Ia):

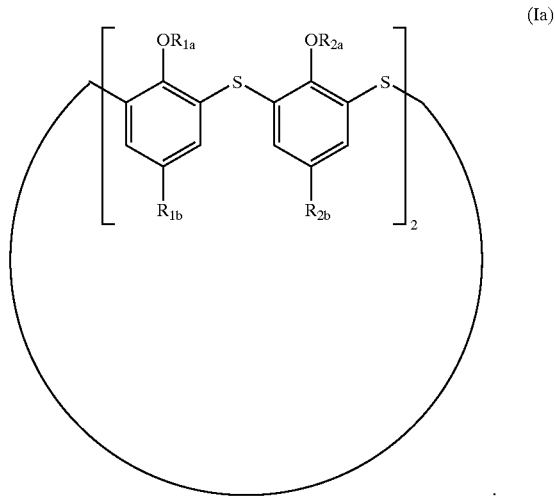

(Ia)

6. The metal (II) complexes according to claim 5, wherein $R_{1a}$ is a hydrogen atom or a $(C_1–C_{12})$ alkyl or $(C_2–C_{12})$ alkenyl group and $R_{2a}$ is a hydrogen atom or a $(C_1–C_{12})$ alkyl or a $(C_2–C_{12})$ alkenyl group.

7. Metal (II) complex according to claim 1, wherein the thiacalix[4]arene is of formula (Ib):

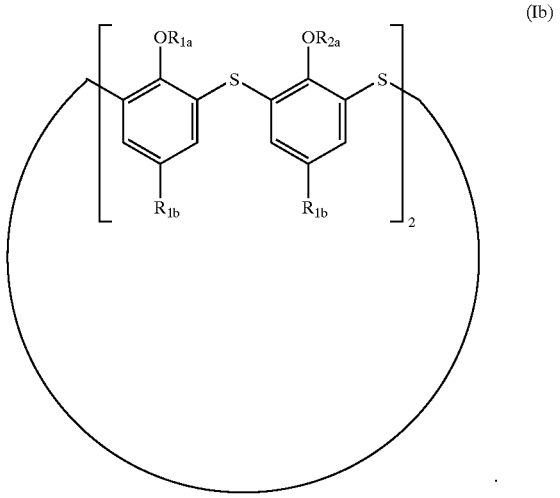

8. Metal (II) complex according to claim 1, wherein the thiacalix[4]arene is of formula (Ic):

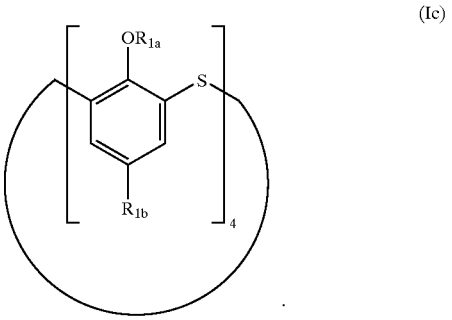

9. Metal (II) complex according to claim 1, wherein the thiacalix[4]arene is selected from the group consisting of:

5,11,17,23-tetrakis(phenylazo)-25,26,27,28-tetrahydroxythiacalix[4]arene, 5,11,17,23-tetrakis(4-nitrophenylazo)-25,26,27,28-tetrahydroxy-thiacalix[4]arene, tetrachlorhydrate de 5,11,17,23-tetraamino-25,26,27,28-tetrahydroxy-thiacalix[4]arene, 5,11,17,23-tetrakis(phenylazo)-25,27-di(4-toluenesulfonyloxy)-26,28-di-hydroxythiacalix[4]arene, 5,11,17,23-tetrakis(4-nitrophenylazo)-25,27-di(4-toluenesulfonyloxy)-26,28-dihydroxythiacalix[4]arene, 5,11,17,23-tetra(4-pyridylimino)-25,26,27,28-tetrahydroxy-thiacalix[4]arene, 5,11,17,23-tetra(phenylethynyl)-25,26,27,28-tetrahydroxy-thiacalix[4]arene, and 5,11,17,23-tetraethynyl-25,26,27,28-tetrahydroxy-thiacalix[4]arene.

10. Metal (II) complex according to claim 1 wherein the metal is a transition metal.

11. Metal (II) complex according to claim 10 wherein the transition metal is copper, silver, zinc, lead or platinum.

12. Metal (II) complex according to claim 11 wherein the transition metal is copper, zinc or nickel.

13. A method for preparing a thiacalix[4]arene having formula (I) as defined in claim 4, wherein at least one of the $R_{1b}$, $R_{2b}$, $R_{3b}$ or $R_{4b}$ substituents is a nitro, —N=CHR$_5$ or —NR$_7$R$_8$ group, wherein R$_7$ is a hydrogen atom and R$_8$ is a hydrogen atom or a —C(O)R$_5$ group with R$_5$ being chosen from the group comprising a $(C_1–C_4)$ alkyl, pyridyl or phenyl group, characterized in that:

a) if $R_{1b}$, $R_{2b}$, $R_{3b}$ and/or $R_{4b}$ is/are a nitro group, the compound (I) is obtained by nitration of the corresponding thiacalix[4]arene, in which said $R_{1b}$, $R_{2b}$, $R_{3b}$ and/or $R_{4b}$ is/are a hydrogen atom, by the action of the nitrogen dioxide or the dinitrogen tetroxide in the presence of an etherized solvent;

b) if $R_{1b}$, $R_{2b}$, $R_{3b}$ and/or $R_{4b}$ is/are an amino group, the compound (I) is obtained by reduction of the respective compound (I), in which said group(s) $R_{1b}$, $R_{2b}$, $R_{3b}$ and/or $R_{4b}$ is/are a nitro group;

c) if $R_{1b}$, $R_{2b}$, $R_{3b}$ and/or $R_{4b}$ is/are a —N=CHR$_5$ group, R$_5$ being a $(C_1–C_4)$ alkyl, phenyl or pyridyl group, the compound (I) is prepared using the respective compound (I), in which said $R_{1b}$, $R_{2b}$, $R_{3b}$ and/or $R_{4b}$ is/are an amino group, by the action of an aldehyde R$_5$—CHO, R$_5$, being a $(C_1–C_4)$ alkyl, pyridyl or phenyl group;

d) if $R_{1b}$, $R_{2b}$, $R_{3b}$ and/or $R_{4b}$ is/are a —NHC(O)R$_5$ group, in which R$_5$ is a $(C_1–C_4)$ alkyl, pyridyl or phenyl group, the compound (I) is obtained using the respective compound (I), in which $R_{1b}$, $R_{2b}$, $R_{3b}$ and/or $R_{4b}$ is/are an amino group, by the action of the acid halogenide Hal-C(O)R$_5$, in which Hal is a halogen atom and R$_5$ and is as hereinbefore defined.

14. The method according to claim 13, wherein at paragraph a), the nitrogen dioxide or the nitrogen tetroxide is formed in situ in the presence of aluminum trichloride and potassium nitrate.

15. The method according to claim 13, wherein at paragraph a) the nitrogen dioxide or the nitrogen tetroxide is in the form of a complex with the etherized solvent.

16. The method according to claim 13, wherein at paragraph a) diglyme, triglyme, tetraglyme or a crown ether is used as the etherized solvent.

* * * * *